United States Patent
Brommersma et al.

(10) Patent No.: US 6,746,395 B2
(45) Date of Patent: Jun. 8, 2004

(54) UROLOGICAL RESECTOSCOPE COMPRISING A CONTACTING DEVICE

(75) Inventors: Pieter Brommersma, Bargteheide (DE); Felix Nussbaum, Hamburg (DE); Thomas Wosnitza, Lüneburg (DE)

(73) Assignee: Olympus Winter & Ibe GmbH, Hamburg (DE)

(*) Notice: Subject to any disclaimer, the term of this patent is extended or adjusted under 35 U.S.C. 154(b) by 74 days.

(21) Appl. No.: 10/111,149
(22) PCT Filed: Aug. 4, 2001
(86) PCT No.: PCT/EP01/09043
§ 371 (c)(1), (2), (4) Date: Jun. 7, 2002
(87) PCT Pub. No.: WO02/17806
PCT Pub. Date: Mar. 7, 2002

(65) Prior Publication Data
US 2002/0183589 A1 Dec. 5, 2002

(30) Foreign Application Priority Data
Aug. 26, 2000 (DE) .......................................... 100 42 095

(51) Int. Cl.[7] .................................................. A61B 1/00
(52) U.S. Cl. ...................... 600/105; 600/106; 600/107; 606/46
(58) Field of Search .................... 606/27–29, 37–41, 606/45–50; 600/105, 106, 107, 101

(56) References Cited

U.S. PATENT DOCUMENTS

| 4,917,621 | A | | 4/1990 | Grossi et al. |
|---|---|---|---|---|
| 4,919,131 | A | | 4/1990 | Grossi et al. |
| 6,105,581 | A | | 8/2000 | Eggers et al. |
| 6,322,494 | B1 | * | 11/2001 | Bullivant et al. ........... 600/104 |
| 6,325,801 | B1 | * | 12/2001 | Monnier et al. ............... 606/46 |
| 6,358,200 | B1 | * | 3/2002 | Grossi ......................... 600/156 |
| 6,605,036 | B1 | * | 8/2003 | Wild ........................... 600/131 |

* cited by examiner

*Primary Examiner*—Beverly M. Flanagan
(74) *Attorney, Agent, or Firm*—Rankin, Hill, Forter & Clark LLP

(57) ABSTRACT

A urological resectoscope having an axially extending shaft tube, the proximal end thereof being fixed to a main body. A sliding body is proximally positioned in relation to the main body, and can slide in a parallel manner in relation to the axis thereof. The sliding body includes a receiver, a fixing device and a contacting device. An electrode which can be subjected to a high frequency, including an electrode carrier having one external, insulated conductive wire, can be positioned in the resectoscope such that it can axially slide beyond the distal end of the shaft tube. In the assembly position, the electrode carrier extends through the shaft tube and the main body into the receiver, and can be fixed thereto by the fixing device and contacted therein by the contacting device. The contacting device defines an opening of the sliding body, the opening completely cutting through in a transversal direction relative to the receiver, and extends perpendicularly relative thereto, to a depth on the other side thereof. In the contacted state, the contacting device includes a clamping connector that is designed for pivotable clamping on a contact section of the electrode carrier.

2 Claims, 2 Drawing Sheets

UROLOGICAL RESECTOSCOPE COMPRISING A CONTACTING DEVICE

BACKGROUND OF THE INVENTION

The term "resectoscope" used herein denotes endoscopic instruments wherein an optics and an electrode support fitted with a distal electrode are configured in a stem tube; and wherein the electrode support has the electrode supported therein in an axially displaceable manner and affixed by its proximal end to a slide block of the resectoscope; and wherein the slide block is manually displaceable in the axial direction when a grip is actuated in order to axially displace the electrode. Resectoscopes of the aforementioned kind are intended foremost for prostate resection but, depending on the particular design, may also be used for other surgical applications.

In prostate resection, the resectoscope is advanced by means of the distal end of the stem tube through the urethra into the inside of the prostate. When the electrode is loaded with high frequency (hf) current, it can be advanced and retracted by manually displacing the slide block, to which the electrode is proximally affixed, for the purpose of cutting tissue. In general, the electrode assumes the shape of a wire loop to resect tissue snippets. However, the electrode also may assume other geometries. For instance, the electrode may be shaped as a button electrode, a roller electrode, a knife electrode or the like, in order to be used for different applications such as coagulation, cutting and the like.

Problems are encountered in this regard in setting up the proper electric contact between the conductor wire applying a current to the electrode and its contact zone in the slide block. The electric contact at the slide block must be set up to an extension cable running to a separate hf generator.

In older designs, electrical contact was set up by means of a clamping screw and simultaneously mechanical affixation of the electrode support was reliably assured in the slide block. However, once the contact site charred, the entire slide block required replacement.

A design of that kind is known from FIG. 3 of both U.S. Pat. Nos. 4,917,621 and 4,919,131. Therein the slide block is fitted with a continuous clearance receiving the plug of the extension cable that makes electrical contact with the electrode support's contact zone, which is freely accessible in the clearance. A clamping element acting on an affixation zone of the electrode support is configured distally from the clearance.

This design offers the advantage of separately mechanically affixing the electrode support and the clamping element on the slide block, as a result of which it is possible to first check the slid block's appropriate mechanical operation. Thereupon, contact may be implemented with the plug. If the contact site should char, only the electrode support and the cable holding the plug would need to be changed. The clamping element and the slide block remain intact because the clamping element is separate.

This design of the known species however incurs the drawback of a rigorous plug guidance within the clearance, entailing a predetermined location on the cable issuing from the plug. This feature is a drawback as regards resectoscopes that, during surgery, for instance in the prostate, must be continuously rotated in order to have the electrode cut at different angles. This desideratum is impeded by the fixed angular position of the hf cable.

SUMMARY OF THE INVENTION

It is an object of the invention to create a resectoscope having improved properties regarding the exit of the hf cable.

In accordance with the present invention, the contact element comprises a clearance that makes the seating fully accessible at three sides. The electrode support received in the seating therefore is freely accessible at a circumferential angle of at least 180° from all sides. The plug is designed to be a clamping plug, which is intrinsically retentive and pivotably engages the electrical contact zone of the electrode support and may be pivoted by a substantially large angle up to 180° and even more about the axis of the electrode support. In the process, when the resectoscope is rotated, the cable suspended from the plug may be hanging from it in swiveling manner, leaving the rotation unhampered.

In further accordance with the present invention, the reliability of clamping of the clamping plug is improved because a groove formed therein assures reliable retention on the electrode support against detachment.

BRIEF DESCRIPTION OF THE DRAWINGS

These and further features of the invention will be apparent with reference to the following description and drawings, wherein.

DETAILED DESCRIPTION OF THE PREFERRED EMBODIMENTS

Figure 1:
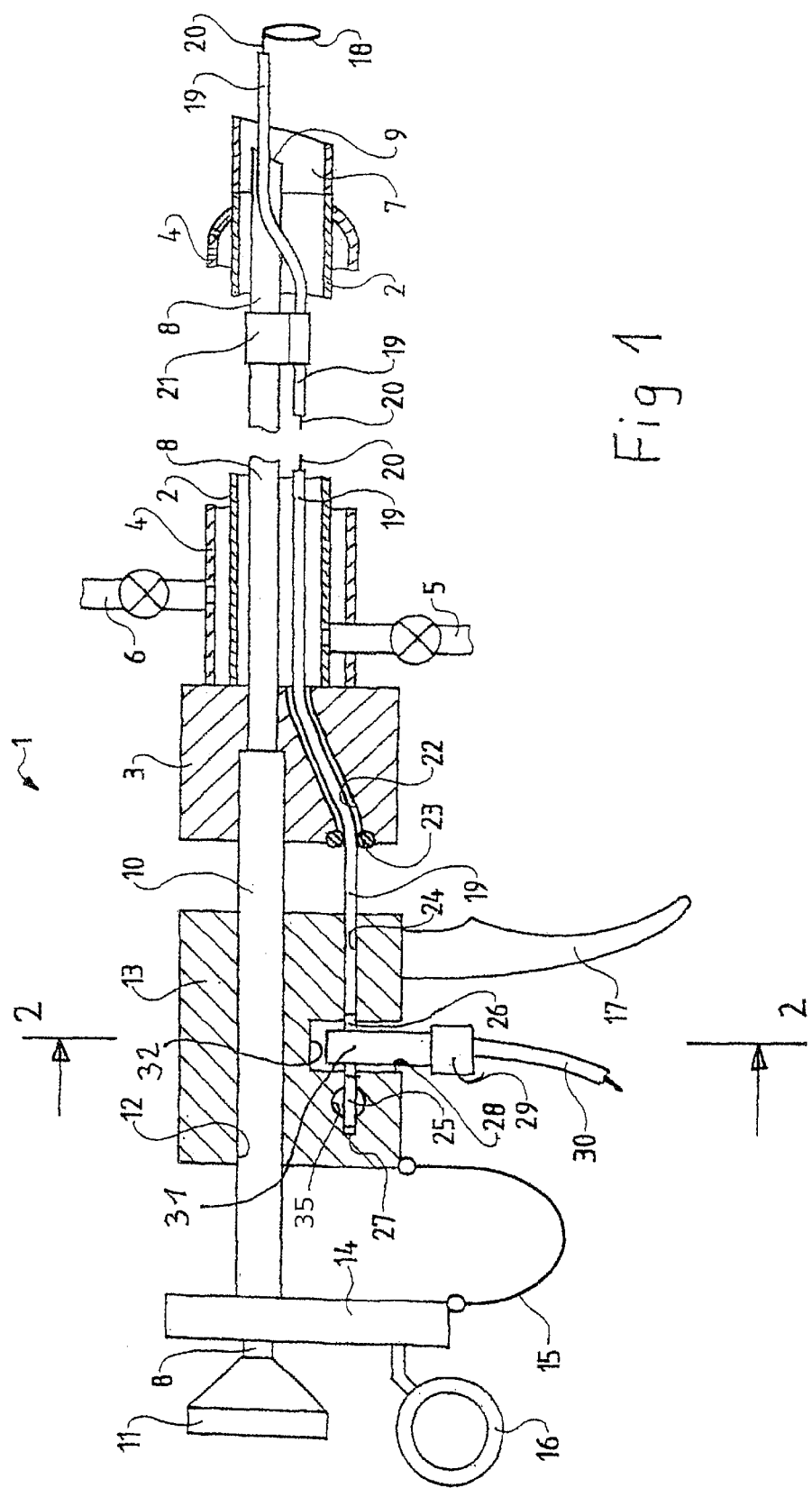
FIG. 1 is a longitudinal section through a resectoscope according to the present invention.
Figure 2:
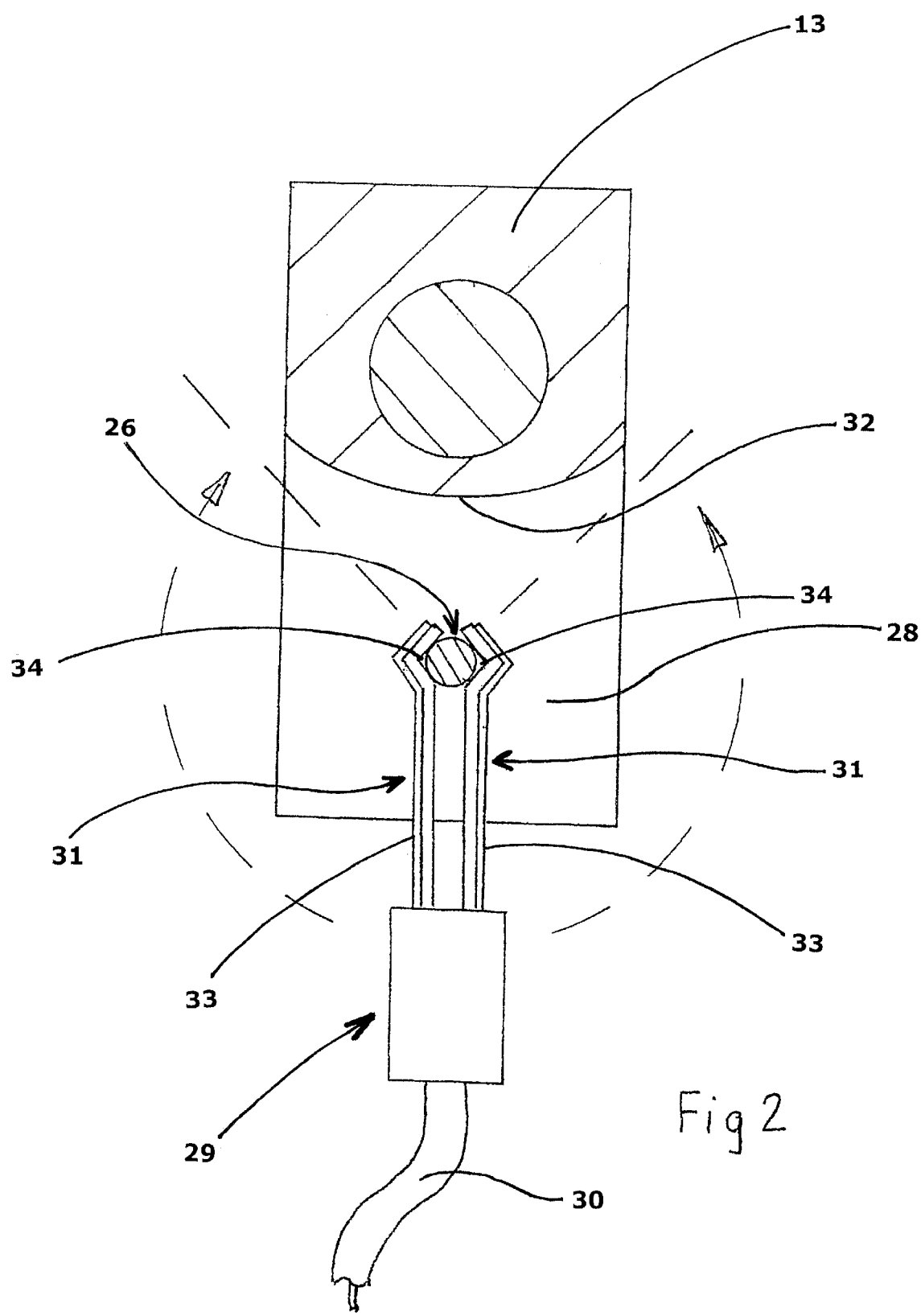
FIG. 2 is a cross-sectional view of the resectoscope as seen along line 2—2 of FIG. 1.

The resectoscope 1 shown in FIG. 1 comprises a stem tube 2 affixed at its proximal end to a main block 3. In manner not shown herein, the stem tube 2 may be detachably affixed by conventional coupling element(s) to the main block 3. An external tube 4 encloses the stem tube 2 and also is affixed to the main block 3, again conventionally, using a coupling element (not shown). The inside of the stem tube 2 serves in conventional manner as a feed duct of continuous irrigation and, as shown by FIG. 2, communicates with outside equipment by a valve-fitted hookup 5, which can be connected to a hose. Another similar hookup 6 for a further hose is connected to the annular gap between the stem tube 2 and the external tube 4 serving as the return duct.

The two tubes 2, 4 are conventionally made of metal. The distal end of the stem tube 2 is conventionally electrically insulating, for instance being in the form of a ceramic end piece 7.

An optics 8 which, in the shown assembled configuration, views by its distal objective 9 the surgical region before the ceramic end piece 7 and proximally crosses the main block 3, runs inside the stem tube 2 and parallel to the axis. The optics 8 further runs through a guide tube 10 affixed in the main block 3 and terminates on the other side of the main block's proximal end in an ocular 11 that may optionally be replaced by a camera.

A slide block 13 is supported in an axially displaceable manner on the guide tube 10 by means of its guide borehole 12. An end plate 14 is affixed to the proximal end of the guide tube 10 and resiliently braces the opposite slide block 13 in this embodiment only by means of the conventional leaf spring 15. A thumb ring 16 is mounted on the end plate 14, and a finger grip 17 is mounted on the slide block 13. Using one hand, the surgeon can seize by his thumb the thumb ring 16 and by his index finger the finger grip 17 and thereby axially displace the slide block 13. Alternatively, in lieu of the "active" drive discussed above, a "passive" drive also may be used whereby the leaf spring 15 is configured between the slide block 13 and the main block 3, and the actuators 16, 17 also are configured at those components.

The shown resectoscope comprises an exchangeable, hf-loaded electrode 18, which in its conventional prostate resection design is in the form of a wire loop of which the plane is orthogonal to the resectoscope axial direction. The electrode 18 is supported by an electrode support 19 in the form of an inner conductor wire 20 enclosed by an outer insulation. In conventional manner, the electrode support 19 rests by a collar 21 in longitudinally displaceable manner on the optics 8 and crosses the stem tube 2 as far as the main block 3. There it crosses a sideways deflected transmission duct 22 fitted with an O ring 23 or the like acting as a liquid seal and exits from the duct's proximal mouth again parallel to the resectoscope axis but at a larger spacing therefrom as far as into a receiving borehole 24 in the slide block 13. Alternatively, the seating borehole 24 may be replaced for instance by a proximally converging aperture, by sideways open slots or the like to seat the electrode support 19.

In its proximal end region, the electrode support 19 comprises an affixation zone 25 that constitutes its end and which is made of sufficient mechanical strength, for instance being solid metal, to reliably mechanically affix the electrode support in that zone. Distally from there, the electrode support 19 comprises a contact zone 26 fitted with an externally electrically conducting outside surface that is connected electrically with the conductor wire 20 of the electrode support.

Moreover, the seating borehole 24, in the form of its proximal end 27, comprises a limit stop for the electrode support 19, the electrode support being insertable into the resectoscope in the direction of the seating borehole 24 as far as said limit stop.

If, in the shown assembled position, the electrode support 19 has been inserted into the seating borehole 24 of the slide block 13 all the way to the limit stop 27, then it will be situated by its affixation zone 26 in a clearance 28 of the slide block 13, the contact zone 26 then being freely externally accessible. In this position, said electrode support can be electrically connected by means of the shown clamping plug 29 at the end of an extension cable 30 running to an omitted hf generator.

The geometry of the clearance 28 is shown enlarged and in greater detail in FIG. 2. FIG. 2 shows that the clearance 28 entirely crosses the slide block 13 transversely to the electrode support 19—shown by its contact zone 26 in FIG. 2—this crossing running from left to right in FIG. 2. In the transverse direction perpendicular thereto, that is, in FIG. 2 from bottom to top, the clearance extends from the underside of the slide block 13 to a height on the other side of the seating borehole, that is beyond the contact zone resting therein, to a surface 32 which is configured spaced away from the contact zone 26, that is from the seating borehole 24. As a result and as indicated in FIG. 2 by the two dashed lines and by the circular arrow, the contact zone 26 within the clearance 28 shall be accessible from all sides within an angle much larger than 180°. The remaining, shaded region of the slide block 13 implements adequate mechanical coupling between the slide block's components axially situated in front of and behind the clearance 28 and allows sliding guidance of the slide block 13 and its guide borehole 12.

The clamping plug 29 is shown in a simple embodiment appropriate for the purposes herein. It comprises two jaws 31 each made of an electrically conducting and mechanically resilient material and, for safety, externally fitted with an insulation 33. At least one of the jaws 31, but in this embodiment both, are fitted at their ends with channels 34 whereby they reliably clamp the contact zone 26 and this with sufficient force of retention to preclude accidental removal of the plug 29 from said contact zone.

For the sake of simplicity, the drawing omits devices by means of which the clamping jaws can be opened against their spring force. For that purpose the jaws 31 illustratively may be fitted at the plug 29 with an omitted opening device. Instead of mounting the jaws in resilient manner, they also may be affixed to the plug 29 in articulating manner for instance like tongs' arms, including an appropriate spring force to secure the clamping force.

An affixation element, which in the present embodiment comprises a transverse borehole 35, is present in the slide block 13. The transverse borehole 35 is optionally threaded on its inside, thereby allowing a tightening screw, to be screwed in, and is configured directly proximally of the clearance 28 in the region of the affixation one 25 of the electrode support 19. Alternatively, the affixation element may be of another design, for instance being fitted with a slider engaging a groove, or a snap-in element, or the like.

When the electrode support 19 is affixed in the slide block 13 and is electrically connected in standard manner, then the entire electrode support 19 together with its electrode 18 may be longitudinally displaced relative to the stem tube 2 by means of the above described sliding motion of the slide block 13. By observing through the optics 8 and provided that hf is applied to the electrode 18, ablating surgery with axial displacement may then be carried out with said electrode.

In order to exchange the electrode 18, the clamping plug 29 is removed and the affixation element is loosened. Thereupon, the electrode support can be fully removed distally from the resectoscope 1. Likewise, a new electrode may be inserted in the proximal direction as far as the limit stop 27, and mechanically affixed and electrically contacted. The exchange of the invention allows first mechanically affixing the electrode support 19 at the transverse borehole 35 and to test its appropriate mechanical performance by moving the slide block 13 back and forth before electrical contact is made with the clamping plug 29.

In the shown embodiment, the electrode support 19 bears an electrode 18 in the form of a conventional resectoscope loop. The shown electrode 18, however, also may be replaced by electrodes exhibiting different geometries such as, for instance, button, pin, roller or knife electrodes, which when loaded with hf shall implement coagulation, vaporization or cutting.

Moreover, bipolar electrodes may be used, where the electrode support 19 therefore bears the two electrodes to be connected to the two output terminals of an hf source. In that case, two conductor wires 20 must be used inside the insulating electrode support 19. In corresponding manner, instead of the single contact zone 26 above, two contact zones must be provided, electrical contacting of which, for instance, may be implemented by means of a double plug. In this case the jaws 31 of the clamping plug may be constituted in each case of two parallel resilient prongs.

In the shown embodiment, the limit stop relating to the insertion of the electrode support 19 is constituted by the end 27 of the seating borehole 24. However, a limit stop also may be fitted onto the clamping element itself, for instance at the tightening screw which shall be screwed into the threaded borehole 35. If the clamping element illustratively were a slider engaging a groove in the affixation zone 25, then a stop also may be fitted on the slider and would cooperate appropriately, for instance, with a corresponding stop on the affixation zone 25.

What is claimed is:

1. A urological resectoscope (1) comprising:
   a main block,
   an axially running stem tube (2), said stem tube having a proximal end and a distal end, said proximal end of said stem tube being affixed to the main block (3),
   a slide block (13) axially displaceable relative to the main block (3) and supported proximally from said main block, said slide block (13) having top and bottom surfaces and including a seat (24), an affixation element and a clamping plug (29),
   an hf-loaded electrode (18), jointly with an electrode support (19) that includes an externally insulated conductor wire (20), being axially displaceable in a supported manner beyond the distal end (7) of the stem tube (2), where, when the resectoscope is in an assembled state, the electrode support (19) runs through the stem tube (2) and through the main block (3) as far as into the seat (24) where it can be affixed by the affixation element,
   wherein the slide block (13) has a clearance (28) fully crossing the slide block and running transverse to the seat (24), the clamping plug (29) engaging the clearance in order to set up an electrical connection with the electrode support (19),
   wherein the clearance (28) runs transversely and perpendicularly to the seat (24) from the bottom surface of the slide block (13) to a height (32) located above the seat (24) and wherein the clamping plug (29) is adapted to allow swiveling clamping action onto an electrical contact zone (26) of the electrode support (19).

2. The resectoscope as claimed in claim 1, wherein the clamping plug (29) comprises two cooperating clamping jaws (31), at least one jaw of said two clamping jaws being fitted at its electrical contact side with a groove running transversely to the at least one jaw.

* * * * *